United States Patent [19]

Gits et al.

[11] 4,235,876

[45] Nov. 25, 1980

[54] LIVE NEWCASTLE DISEASE VIRUS VACCINE

[75] Inventors: Jacqueline Gits, La Hulpe; Nathan Zygraich, Brussels, both of Belgium

[73] Assignee: SmithKline-Rit, Belgium

[21] Appl. No.: 899,424

[22] Filed: Apr. 24, 1978

[30] Foreign Application Priority Data

Apr. 25, 1977 [BE] Belgium ............................... 853923

[51] Int. Cl.$^2$ ..................... A61K 39/12; A61K 9/12; C12K 7/00

[52] U.S. Cl. ......................................... 424/89; 424/43; 424/45; 424/46; 435/237

[58] Field of Search .................. 424/89, 43, 45, 46; 195/1.3; 435/237

[56] References Cited

U.S. PATENT DOCUMENTS

| | | | |
|---|---|---|---|
| 2,767,117 | 10/1956 | Crawley .................................. | 424/89 |
| 2,798,835 | 7/1957 | Markham et al. ..................... | 424/89 |
| 3,548,054 | 12/1970 | Bowen et al. ........................... | 424/89 |
| 4,053,583 | 10/1977 | Gits et al. ............................... | 424/89 |

FOREIGN PATENT DOCUMENTS

851880 8/1977 Belgium .

OTHER PUBLICATIONS

Vet. Bull. (1976) 46, 12, 6995, P. Danchev et al.
Vet. Bull. (1972) 42, 7, 3874, N. Lagutkin et al., "Aerosol immunization of fowls against Newcastle Disease".
Vet. Bull. (1971), I. Bondarenko et al., 41, 7, 3370, "Onset and duration of immunity in chicks immunized against Newcastle disease by the aerosol method".
Vet. Bull., (1975), 45, 1, 149, G. Schulze-Rehm et al., "Studies on spray vaccination against Newcastle disease".
Vet. Bull., (1974), 44, 9, 4434, G. Quaglio et al., "Immunity induced in chickens by Newcastle disease virus, LaSota strain, in relation to the routes of exposure".
Vet. Bull., (1974), 44, 1, 142, I. Bondarenko et al., "Effectiveness of immunization against Newcastle disease (by inhalation, nasal and oral routes using LaSota and B1 strains".
Vet. Bull., (1974) 44, 6, 2749, G. Schulze-Rehm, "Spray vaccination against Newcastle disease using the Hitchner B1 and LaSota strains".
Vet. Bull., (1976) 46, 10, 5687, P. Villegas et al., "Aerosol vaccination against Newcastle Disease".
Vet. Bull. 46, 10, 5688, H. Pieper.
Vet. Bull. (1976) 46, 2, 675, C. Roman, "Morphologic and genetic heterogeneity in egg and monolayer propagated NDV".
Vet. Bull. (1976) 46, 1, 115, S. Yachida et al., "The effect of overlay medium on plaque formation of tissue culture-attenuated Newcastle disease vaccine virus".
Vet. Bull., (1976) 46, 8, 4397, M. Bansal et al., "Propagation and characterization of NDV in chicken embryo fibroblast and kidney cell culture".
Vet. Bull. (1973) 43, 6, 2531, Z. Larski et al.
R. E. Gough et al., Vet Rec., 95 (12), 263–265 (1974).
Gits et al., Paper delivered at Internat'l. Symposium of the Worldwide Assoc. of Veterinarians, Microbiologists, Immunologists, etc., Held in Tunis, Aug. 8–Sep. 2, 1976.
Nagai et al, Virology 72: 494, 1976.

*Primary Examiner*—Donald G. Daus
*Assistant Examiner*—M. C. Eakin
*Attorney, Agent, or Firm*—Janice E. Williams; Alan D. Lourie

[57] ABSTRACT

The invention relates to an avian vaccine and to the preparation thereof.

The vaccine according to the invention is a Newcastle disease virus vaccine. Its active ingredient is the P/77/8 NDV strain.

The vaccine of the invention is useful in the prevention of Newcastle disease by administration to chickens in the form of an aerosol.

5 Claims, No Drawings

LIVE NEWCASTLE DISEASE VIRUS VACCINE

This invention relates to a process for preparing an improved Newcastle disease virus (NDV) strain valuable for vaccinal use and to the live vaccine containing it.

Live NDV vaccines containing either lentogenic or mesogenic strains and administrable by various routes are known. Examples of known vaccinal NDV strains are the La Sota and Hitchner B1 strains. For administration, the NDV vaccines are for example either suspended in the drinking water or administered either as ocular or nasal drops or as aerosol.

The preferred method of vaccination for mass immunization against NDV is the application of live lentogenic viruses such as the La Sota or Hitchner B1 strains in the form of an aerosol but the aerosol administration of these strains has been shown to be associated with rather important morbidity for young chickens, more particularly for very young chickens (R. E. GOUGH and W. H. ALLAN, Vet. Rec. 95 (12), 263–65, 1974).

In our Belgian patent No. 851 880, we described improved vaccines against Newcastle disease and administrable in the form of an aerosol, the said vaccines comprising an effective dose (dose inducing 100% seroconversion among the vaccinated animals) of an attenuated temperature-sensitive and cold-adapted strain obtained from a Newcastle disease virus strain by ultraviolet or nitrous acid mutagenesis thereof.

The term "cold strain" refers to a strain showing a markedly higher growth than the parent strain at a temperature lower than the normal growth temperature of the virus and the "temperature-sensitive" expression refers to a modified strain the growth of which at a relatively high temperature (more particularly at a temperature close to the internal temperature of the host) is definitely inhibited, whereas the growth of the parent strain is not modified at this same temperature.

An example of such vaccine is the one comprising an effective dose of the Newcastle disease virus P/76/5 strain deposited at the World Health Organization Collaborating Centre for Collection and Evaluation of Data on Comparative Virology at the Institut für Medizinische Mikrobiologie, Infektionsund Seukenmedizin der Ludwig-Maximilians Universität (Müchen, West Germany).

By comparison with the vaccine comprising the parent Newcastle disease virus strain (i.e. the La Sota strain), the vaccine comprising the Newcastle disease virus P/76/5 mutant strain was shown to present a considerably reduced morbidity upon administration in the form of an aerosol to 1 to 8 day-old chickens and an effective dose of the vaccine was shown to be $10^{7.5} EID_{50}$ (infective dose in 50 percents of the inoculated eggs) per cubic foot of air.

In the above cited patent specification, the P/76/5 strain was described as a cold-adapted and temperature-sensitive mutant strain obtained from the NDV La Sota strain and, in a further paper entitled "Potential as an aerosol vaccine of an improved Newcastle disease vaccine derived from the La Sota strain. I. In vitro studies " presented by inventors at the International Symposium of the Worldwide Association of Veterinarians, Microbiologists, Immunologists and Specialists in infectious illnesses, held in Tunis from Aug. 8 to Sept. 2, 1976, the P/76/5 strain was further characterized regarding its infective properties in chicken embryo fibroblasts (CEF). A summary of this communication was published by the sponsors of this Symposium (A.M.V.-M.I., Maisons-Alfort, France).

These characteristics may indeed reflect the attenuation degree of a Newcastle disease virus strain. As shown by NAGAI ET AL. in Virology 72: 494, 1976, a correlation does exist between the degree of pathogenicity of different NDV strains and their infectivity in cell cultures. By definition, the attenuated strains present a reduced infectivity but this infectivity can be enhanced by treatment of the virus with trypsin.

We have shown that the infectivity of strain P/76/5 on chicken embryo fibroblasts is significantly lower than the one of the La Sota parent strain and that the enhancement of infectivity in the presence of trypsin is significantly higher for the P/76/5 strain than for the La Sota strain. This characteristic can be correlated with the stronger attenuation of the P/76/5 strain.

We have now found and this is the object of the present invention that, after passaging the NDV P/76/5 strain twice on chicken embryo fibroblasts (CEF) at a non-permissive temperature—more particularly at 41° C.—it was possible to isolate a strain lacking the cold and temperature-sensitive characteristics of the P/76/5 strain but still showing the same reduced infectivity in CEF and the same ability of activation by trypsin.

The strain of Newcastle disease virus obtained according to the process of this invention has been deposited at the WHO Collaborating Centre for Collection and Evaluation of Data on Comparative Virology where it received accession number P/77/8.

Surprisingly, the so-obtained strain was found markedly more immunogenic than its cold and temperature-sensitive parent, the P/76/5 strain.

We have found indeed that the effective dose (dose inducing 100 percents seroconversion in the vaccinated animals) of a vaccine comprising the strain of the present invention—i.e. the NDV P/77/8 strain—is $10^6 EID_{50}$ per cubic foot of air, i.e. ten times lower than the effective dose of a vaccine comprising the parent P/76/5 strain.

Thus, the vaccine of this invention is an improved vaccine against Newcastle disease and administrable in the form of an aerosol, comprising a pharmaceutical diluent for aerosol administration and an effective dose of the NDV P/77/8 strain.

The improved NDV vaccine of the invention is prepared by a process which comprises passaging twice in CEF at a non-permissive temperature the P/76/5 NDV strain, harvesting the strain obtained from the second passage and preparing therewith according to any technique known to the art a live vaccine administrable in the form of an aerosol, the said vaccine being preferably freeze-dried and more particularly freeze-dried after addition of a stabilizer.

For instance, for large scale production of a vaccine according to the invention, the NDV P/77/8 strain is grown in specific-pathogen-free (SPF) embryonated chicken eggs at a temperature between 34° and 37° C. from which the virus is harvested e.g. after a three-day incubation period.

The harvested virus is then preferably supplemented with a stabilizing solution-examples of stabilizing solution are peptone or arginine or sucrose, or preferably mixtures thereof, in water-distributed in glass vials and freeze-dried. The vaccine is kept in freeze-dried form in tightly-stoppered vials and rehydrated before administration.

The improved vaccine of this invention can be mixed with any other live vaccine or vaccines against avian respiratory diseases—e.g. avian infectious bronchitis vaccine-administrable in the form of an aerosol.

For vaccination, the vaccine is extemporaneously rehydrated and administered to the chickens according to the well-known method of NDV vaccine administration in the form of an aerosol.

According to this embodiment, the invention relates to the method for immunizing chickens against Newcastle disease virus, the said method consisting of administering to the said chickens in the form of an aerosol and per cubic foot of air at least $10^6 EID_{50}$ of NDV P/77/8 strain as hereinabove described.

The following examples illustrate the present invention and should not be construed as limiting its scope.

EXAMPLE 1

A sample of the P/76/5 strain (0.2 ml of a suspension titrating $10^5 EID_{50}$/ml) is inoculated into chicken embryo fibroblasts (CEF) monolayers ($10^6$ cells). The inoculated cells are covered with minimum Eagle's medium supplemented with 2% (v/v) of foetal calf serum, incubated at 41° C. for 4 days and the supernatant is then harvested.

A 0.2 ml aliquot of the non-diluted harvest having a titer of $10^{2.5}TCID_{50}/ml$ (infectious dose in 50% of the cell cultures) is inoculated into CEF monolayers and the inoculated cells are incubated as indicated for the first passage.

The harvested supernatant from the second passage is inoculated into specific-pathogen-free (SPF) eggs and cloned by end-point dilution is 35° C.

A seed-stock of the obtained clone named P/77/8 is prepared by allowing said clone to grow in SPF eggs at 35° C. for 3 days.

EXAMPLE 2

Characterization of the NDV P/77/8 strain

(a) Temperature-sensitivity

To differentiate P/77/8 from P/76/5 and La Sota strains, each of these strains was separately inoculated into CEF monolayers and the inoculated cells were incubated for 5 days at 35° C. and 41° C. respectively.

The infectious titres are given in the following Table I which shows that the P/77/8 strain is lacking the thermosensitivity of the P/76/5 strain.

TABLE I

| Strain | Infectious titre^x at: 35° C. | 41° C. | Δ 35° C./41° C. |
|---|---|---|---|
| La Sota | 5.1 | 5.0 | 0.1 |
| P/76/5 | 5.4 | 3.6 | 1.8 |
| P/77/8 | 5.4 | 5.3 | 0.1 |

^x expressed in $log_{10}TCID_{50}/0.05$ ml.

(b) Cold-adapted character

To test the procedure or absence of the "cold" character, embryonated eggs were inoculated with $10^{3.5}EID_{50}$ of virus and incubated at either 26° C. or 35° C. The virus was harvested after 2 days and titrated on CEF at 35° C. in the presence of trypsin (5 μg/ml).

TABLE II

| Strain | Virus yield at 26° C. | 35° C. |
|---|---|---|
| La Sota | 0.5 | 8.4 |
| P/76/5 | 1.7 | 5.9 |
| P/77/8 | 0.7 | 6.6 |

^x yield titrated on CEF and expressed in $log_{10}TCID_{50}/0.05$ ml.

As shown in Table II, the P/77/8 strain has lost the cold-adapted character of its parent P/76/5 strain.

(c) Evaluation of the infectivity of the P/77/8 strain in CEF and influence of trypsin on this infectivity.

The infectivity of the P/77/8 strain has been determined in CEF and compared to the infectivity of other strains the pathogenicity degree of which is well known (NAGAI Y. ET AL. Virology 72:494, 1976).

The lowering of infectivity in CEF is expressed by the increase of the difference between infectious titre in CEF and the infectious titre in eggs.

The influence of trypsin on infectious titre of these different strains in CEF has also been determined. The results are given in Table III.

TABLE III

| Strain | Difference between infectious titre in eggs and CEF^x | Difference between infectious titre in CEF^x in the presence or absence of trypsin |
|---|---|---|
| Essex | 0.8(±0.1) | −0.1(±0.4) |
| Herts | 1.1(±0.2) | 0.0(±0.1) |
| La Sota | 2.1(±0.3) | 1.4(±0.2) |
| Bl | 2.1(±0.2) | 1.8(±0.1) |
| Ulster | 3.2(±0.4) | 2.3(±0.1) |
| P/77/8 | 3.5(±0.2) | 2.4(±0.2) |

^x infectious titre in $log_{10}ID_{50}/0.1$ ml (infectious dose in 50% of CEF; the figures between brackets express standard deviation.)

Table III clearly indicates that the evaluated properties allow to distribute the different strains in three separate classes and that the P/77/8 strain is markedly different from the La Sota strain. Its infectivity in CEF is significantly more reduced and it is more sensible to activation by trypsin.

(d) Thermolability of the hemagglutinin

To test the thermolability of its hemagglutinin, the P/77/8 strain was exposed to different temperature for different durations. Table IV shows the results of the test for the P/77/8 strain, a pathogenic strain (Essex) and an attempted one (La Sota) respectively.

TABLE IV

| Duration of exposure at | | Thermolability of the hemagglutinin : reciprocal of hemagglutination titre. Essex | La Sota | P/77/8 |
|---|---|---|---|---|
| 22° C. : | 0 min. | 256 | 1024 | 1024 |
| | 60 min. | 128 | 1024 | 1024 |
| 50° C. : | 10 min. | 256 | 256 | 512 |
| | 20 min. | 256 | 64 | 256 |
| | 30 min. | 256 | 8 | 8 |
| | 40 min. | 256 | <2 | <2 |
| | 60 min. | 256 | <2 | <2 |
| 56° C. : | 2 min. | 256 | 256 | 128 |
| | 5 min. | 256 | <2 | <2 |
| | 10 min. | 256 | <2 | <2 |

It appears that the P/77/8 strain's hemagglutinin has the same thermolability as the La Sota's hemagglutinin.

(e) pH sensitivity

To compare the pH sensitivity of the P/77/8 and the La Sota strains, both were exposed to various pH at 35° C. for 4 hours. Their residual infectious titres are recorded in Table V.

TABLE V

| | pH Sensitivity | |
|---|---|---|
| | Infectious titre* | |
| pH | La Sota | P/77/8 |
| | initial titre : 5.5 | |
| 7 | 5.5 | 5.5 |
| 5 | 5.4 | 5.2 |
| 3 | 0 | 0 |

*expressed in $\log_{10} TCID_{50}/0.05$ ml in CEF.

As shown, the P/77/8 and La Sota strains have comparable pH sensitivity.

EXAMPLE 3

The virus from the seed-stock obtained in Example 1 is cultivated in SPF embryonated eggs at 35° C. for 3 days and the harvested supernatant is supplemented with a stabilizing solution consisting of peptone (10% w/v), arginine (3% w/v) and sucrose (5% w/v). The mixture is distributed in 5 ml glass vials containing each $10^6 EID_{50}$ per ml and freeze-dried and the vials are tightly stoppered to constitute multiple doses of vaccine for administration in aerosol form.

EXAMPLE 4

"In vivo" trials with the P/77/8 strain

(a) Innocuity tests

For testing the innocuity of the P/77/8 strain, day-old SPF chickens maintained in an isolation unit were vaccinated with 50 ml of the vaccine ($10^{7.5} EID_{50}/0.5$ ml), using a Turbair aerosol generator (Turbair Ltd., Britannica Works, Waltham Abbey, Essex, Great Britian) and observed for 10 days. A group of SPF day-old chickens were vaccinated in the same conditions with the La Sota strain, as control. The results are summarized in following Table VI.

TABLE VI

| | Innocuity of the P/77/8 strain | | | |
|---|---|---|---|---|
| Strain | Number of animals | Pathogenicity Index* | mean | 95% confidence limits on the mean |
| La Sota | 20 | 0.45 | 0.352 | 0.15–0.554 |
| | 10 | 0.20 | | |
| | 9 | 0.58 | | |
| | 10 | 0.20 | | |
| | 20 | 0.33 | | |
| P/77/8 | 10 | 0.00 | 0.020 | 0.000–0.069 |
| | 20 | 0.02 | | |
| | 10 | 0.04 | | |

TABLE VI-continued

| | Innocuity of the P/77/8 strain | | | |
|---|---|---|---|---|
| Strain | Number of animals | Pathogenicity Index* | mean | 95% confidence limits on the mean |
| | 10 | 0.04 | | |

*pathogenicity index (PI) calculated for a 10-day post-inoculation observation period.

$$(PI) = \frac{\text{sum of scores}}{\text{number of observations}} \text{ with the score system} \begin{cases} \text{morbidity} = 1 \\ \text{mortality} = 2 \end{cases}$$

The results of Table VI indicate that, for administration in the form of aerosol, the P/77/8 strain is more attenuated for day-old chickens than the La Sota strain.

(b) Dose range

To determine the dose range of the P/77/8 strain in the vaccines SPF day-old chickens (10 birds per group) were vaccinated with various doses of vaccine.

The following Table VII shows the seroconversion rate and the geometric mean titre (GMT) of HI of seropositive birds, 3 weeks post vaccination.

TABLE VII

| Dose ($\log_{10} ID_{50}$) per cubic foot of air | Percentage of seroconversion among animals vaccinated with strain | | | GMT ($\log_2$ HI) of seropositive animals vaccinated with strain | | |
|---|---|---|---|---|---|---|
| | La Sota | P/76/5 | P/77/8 | La Sota | P/76/5 | P/77/8 |
| 4.5 | 10 | NT | 0 | (5.0) | NT | NT |
| 5.5 | 90 | 0 | 20 | 6.6 | NT | (3.5) |
| 6.0 | NT | 40 | 100 | NT | 4.2 | 4.6 |
| 6.5 | 100 | 70 | 100 | 7.8 | 4.1 | 5.7 |
| 7.0 | NT | 100 | 100 | NT | 4.4 | 6.4 |
| 7.5 | 100 | 100 | 100 | 7.9 | 6.6 | 7.3 |

NT : not tested.

The figures between brackets were obtained on less than five animals.

From Table VII it appears that the dose inducing 100% seroconversion (effective dose) for the NDV vaccine containing the P/77/8 strain is $10^6 EID_{50}$.

We claim:
1. An improved vaccine against Newcastle disease and administrable in the form of an aerosol comprising an effective dose of the Newcastle disease virus P/77/8 strain and a pharmaceutical diluent for aerosol administration.
2. An improved re-hydratable freeze-dried form of a vaccine according to claim 1 which the vaccine is supplemented with a stabilizer.
3. A process for preparing an improved vaccine against Newcastle disease and administrable in the form of an aerosol which comprises passaging twice in CEF at 41° C. the P/76/5 NDV strain, harvesting the strain obtained from the second passage and preparing therewith according to any technique known to the art a live vaccine administrable in the form of an aerosol.
4. A process according to claim 3, wherein the vaccine is supplemented with a stabilizer and freeze-dried.
5. A method of immunizing chickens against Newcastle disease consisting in administering to said chickens in the form of an aerosol an effective dose of a vaccine according to claim 1.

* * * * *